United States Patent [19]

Botvidsson et al.

[11] Patent Number: 4,611,604
[45] Date of Patent: Sep. 16, 1986

[54] BIPOLAR ELECTRODE FOR MEDICAL APPLICATIONS

[75] Inventors: Lars Botvidsson, Jaerfaella, Sweden; Konrad Mund, Uttenreuth, Fed. Rep. of Germany

[73] Assignee: Siemens Aktiengesellschaft, Berlin & Munich, Fed. Rep. of Germany

[21] Appl. No.: 569,980

[22] Filed: Jan. 11, 1984

[30] Foreign Application Priority Data

Jan. 11, 1983 [DE] Fed. Rep. of Germany ....... 3300694

[51] Int. Cl.$^4$ .............................................. A61N 1/04
[52] U.S. Cl. .................................. 128/784; 128/419 P
[58] Field of Search ..................... 128/419 P, 784–788

[56] References Cited

U.S. PATENT DOCUMENTS

| 3,981,309 | 9/1976 | Cannon | 128/784 |
|---|---|---|---|
| 4,033,357 | 7/1977 | Helland et al. | 128/785 |
| 4,280,514 | 7/1981 | MacGregor | 128/786 |
| 4,281,668 | 8/1981 | Richter et al. | 128/784 |
| 4,281,669 | 8/1981 | MacGregor | 128/784 |
| 4,440,178 | 4/1984 | Bussard et al. | 128/419 P |

FOREIGN PATENT DOCUMENTS

| 0043461 | 1/1982 | European Pat. Off. |
| 2165622 | 7/1973 | Fed. Rep. of Germany . |
| 2613072 | 10/1977 | Fed. Rep. of Germany . |
| 2922354 | 12/1980 | Fed. Rep. of Germany . |
| 3046732 | 8/1981 | Fed. Rep. of Germany . |

OTHER PUBLICATIONS von Sturm, "Implantable Electrodes", Topics in Biochemistry and Bioenergetics, vol. 3, 1979, pp. 191–241.
Mund et al, "Development of a Non-Polarizable Stimulating Electrode for Implantable Cardiac Pacemakers", Siemens Forsch.-u. Entwickl.-vol. 8, No. 4, pp. 227–234.
Bisping, "Neue Schrittmachersonden-ein Bericht aus Montreal", Biomedizinische Technik, vol. 25, Nos. 7, 8, Jul./Aug. 1980, Berlin, pp. 170–175.

Primary Examiner—William E. Kamm
Attorney, Agent, or Firm—Hill, Van Santen, Steadman & Simpson

[57] ABSTRACT

In order to improve the mechanical properties in the area of the passive electrode given bipolar electrodes, the active region of the passive electrode exhibits a surface layer that has a high double layer capacitance at the phase boundary with the body fluids. The size of the passive electrode can be considerably reduced as a result. Particularly suitable as the surface layer is a porous layer consisting of a carbide, nitride or carbonitride of at least one of the metals titanium, vanadium, zirconium, niobium, molybdenum, hafnium, tantalum or tungsten. A layer of activated carbon with a surface having a porous microstructure or, in the simplest case, a roughened surface are also suitable.

11 Claims, 3 Drawing Figures

BIPOLAR ELECTRODE FOR MEDICAL APPLICATIONS

CROSS-REFERENCE TO RELATED APPLICATIONS

Reference is made to a copending application U.S. Ser. No. 569,832 filed Jan. 11, 1984 in the names of Konrad Mund, Helmut Freller and Friedrich Hoerauf, entitled "Electrode for Medical Applications" and to a copending application U.S. Ser. No. 569,979 filed Jan. 11, 1984 in the names of Hakan Elmqvist and Konrad Mund, entitled "Heart Pacemaker System".

BACKGROUND OF THE INVENTION

The invention relates to a bipolar electrode for medical applications, particularly an implantable heart pacemaker electrode, comprising an insulated conductor system, at least one active electrode and a passive electrode disposed along the conductor system at an interval from said active electrode.

In the case of unipolar heart pacemaker treatment, problems often occur with muscle stimulations and/or muscle inhibitions at the housing of the heart pacemaker, said housing usually representing the passive electrode in the electrode system. A possible solution of this problem, as known, resides in utilizing a bipolar electrode system, i.e. of disposing the passive electrode in the proximity of the active electrode(s) inside of the heart. There is an effort to reduce the impedance of the electrode system due to the small distance between the active and passive electrodes. Known passive electrodes consist, for example, of a cylindrical body of a platinum/iridium alloy having a surface area of approximately 50 mm$^2$. Due to the relatively low double layer capacitance of platinum/iridium (10 $\mu$F/cm$^2$, 1 kHz), this electrode must have such a large surface area in order to keep the polarization losses within justifiable limits.

Considerable mechanical problems arise, however, due to the large dimensions of the passive electrode. Imagining, for example, an insulated electrical conductor 3 mm in diameter, then the cylindrical body of the passive electrode must be about 5 mm long in order to have the required surface area. That produces a considerable stiffening of the otherwise extremely flexible electrical conductor in the proximity of the active electrode. When, for example, it is a matter of a heart ventricle electrode which is to be applied in the tip of the left heart ventricle, then the passive electrode likewise lies in this heart ventricle. Given the large number of bends that this electrical conductor is exposed to, such a pronounced stiffening represents a geat burden that increases the risk that damage to the insulation or a break of the conductor will occur in the proximity of the stiffening.

SUMMARY OF THE INVENTION

A principal object of the present invention is to reduce the surface area of the passive electrode given unaltered or even reduced polarization losses and to thus considerably reduce the mechanical stresses of the electrode in this region.

This object is inventively achieved in that at least the active region of the passive electrode has a surface layer that provides a high double layer capacitance at the phase boundary with the body fluids. This high double layer capacitance insures a low electrochemical impedance and produces only a slight polarization rise during the stimulation pulses. This reduction in electrochemical impedance and consequent reduction in polarization losses can be exploited for reducing the surface area of the passive electrode and thus reducing the mechanical stresses of the electrode.

To that end, the passive electrode can advantageously have a roughened surface or consist overall of a porous material, for example of a sintered metal alloy. It is likewise possible to provide the surface of the passive electrode with a layer of activated glassy carbon that has an extremely high double layer capacitance of up to 0.1 F/cm$^2$.

A particularly advantageous passive electrode is obtained in that the surface layer is provided by a porous layer of a carbide, nitride or carbonitride of at least one of the metals titanium, vanadium, zirconium niobium, molybdenum, hafnium, tantalum or tungsten. The porous carbide, nitride or carbonitride layers are situated on an electrically conductive carrier material, for example platinum, titanium or a metal alloy such as Elgiloy. The double layer capacitances attainable therewith and the surface area reductions possible as a result thereof lie on approximately the same order as given by glassy carbon layers. In terms of manufacturing technology, however, these porous carbide, nitride and carbonitride layers are to be preferred.

In order to avoid material-associated differential potentials, it is provided in another development of the invention that a dense nonporous sealing layer of a material corresponding to the material of the porous layer is situated between the carrier material and said porous layer.

The double layer capacitances of the inventive, passive electrodes are higher than those of known electrodes by a factor of about 10 through 100 so that a significant reduction of the surface area of the passive electrode is possible. This electrode practially shrinks to a narrow ring that hardly changes the mechanical properties of the conductor system at all, i.e. the high elasticity of the electrode line is largely guaranteed even in the area of the passive electrode.

In addition to the improved mechanical properties, the electrochemical impedance of the overall electrode system can also be reduced with the assistance of the inventive passive electrode depending on the size of the reduction in surface area that is selected, whereby the sensitivity of the system is further enhanced.

An examplary embodiment of the inventive bipolar electrode system is described and explained below with reference to the accompanying sheet of drawings; and other objects, features and advantages will be apparent from this detailed disclosure and from the appended claims.

DETAILED DESCRIPTION

Figure 1:
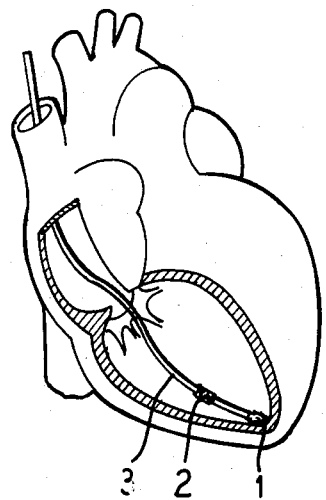
FIG. 1 is a somewhat diagrammatic illustration of a bipolar electrode system in accordance with the present invention and showing the passive electrode emplaced in the left ventricle of the heart.
Figure 2:
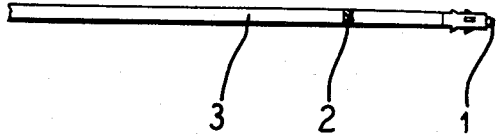
FIG. 2 is a somewhat more detailed showing of the implanted electrode system of FIG. 1.

FIG. 1 shows a bipolar electrode system wherein an implanted heart pacemaker external to the heart is connected with the implanted electrodes 1 and 2 via a flexible cable 3. The passive electrode 2 is shown as being implanted in the same chamber of the heart as the active stimulation electrode 1. The passive electrode 2 is disposed along the insulated covering of the cable 3 in proximity to the active electrode 1 and inside of the heart and is electrically connected with one of the conductors of cable 3 in any suitable manner. The insulated covering of cable 3 may have an outside diameter of three millimeters, and as indicated in FIG. 2, the length of the cylindrical active region 2 of the passive electrode may be less than the outside diameter of the cable 3 to which the passive electrode is applied. Thus the passive electrode 2 which is of any of the forms described herein does not result in a material stiffening of the otherwise extremely flexible electrical cable 3 in the proximity of the active electrode 1.

Specifically, the passive electrode 2 in each of the forms described herein is preferably in the shape of a narrow ring having a length which is a minor fraction (e.g. one-tenth) of five millimeters and hardly changes the mechanical properties of the cable 3 so that the high flexibility of the cable 3 is largely guaranteed even in the area of the passive electrode 2.

The drawings are to be understood as illustrating each of the embodiments defined in the claims.

Figure 3:
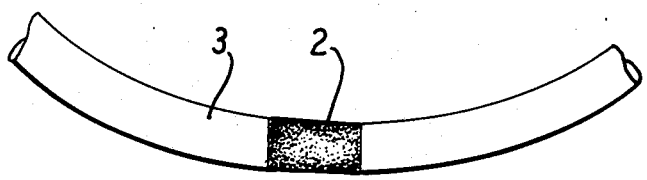
FIG. 3 is a partial further enlarged view of illustrating an active region of the passive electrode applied to the insulated covering of the electrode cable of FIGS. 1 and 2.

In FIGS. 1-3, the passive electrode region 2 can advantageously have a roughened surface or consist overall of a porous material, for example of a sintered metal alloy. It is likewise possible to provide the surface of the passive electrode with a layer of activated glassy carbon that has an extremely high double layer capacitance of up to 0.1 F/cm$^2$.

A particularly advantageous passive electrode is obtained in that the surface layer is provided by a porous layer of a carbide, nitride or carbonitride of at least one of the metals titanium, vanadium, zirconium, niobium, molybdenum, hafnium, tantalum or tungsten. The porous carbide, nitride or carbonitride layers are situated on an electrically conductive carrier material, for example platinum, titanium or a metal alloy such as Elgiloy. The double layer capacitances attainable therewith and the surface area reductions possible as a result thereof lie on approximately the same order as given by glassy carbon layers. In terms of manufacturing technology, however, these porous carbide, nitride and carbonitride layers are to be preferred.

In order to avoid material-associated differential potentials, it is provided in another development of the invention that a dense nonporous sealing layer of a material correspondig to the material of the porous layer as situated between the carrier material and said porous layer.

The double layer capacitances of the inventive, passive electrodes are higher than those of known electrodes by a factor of about 10 through 100 so that a significant reduction of th surface area of the passive electrode is possible. This electrode practially shrinks to a narrow ring (as shown in FIG. 2) that hardly changes the mechanical properties of the conductor system at all, i.e. the high elasticity of the electrode line 3 is largely guaranteed even in the area of the passive electrode 2.

In addition to the improved mechanical properties, the electrochemical impedance of the overall electrode system can also be reduced with the assistance of the inventive passive electrode depending on the size of the reduction in surface area that is selected, whereby the sensitivity of the system is further enhanced.

The thin, porous nitride, carbide or carbonitride layers are preferably applied by means of ion plating, i.e. by means of physical vapor deposition onto the carrier material such as titanium or platinum serving as the substrate. Dense nonporous sealing layers can thereby first be deposited followed by porous layers of the same material in a continuous fabrication process by means of changing the vapor pressures.

Elgiloy is a corrosion resistant alloy having the following components: cobalt, chromium, nickel, iron, molybdenum, manganese, carbon and beryllium.

A high double layer capacitance is a capacitance between the passive electrode at the active region and bodily fluid which permeates the active region which lies in the range from about ten millifarads per centimeter squared and about one hundred millifarads per centimeter squared when measured with a pulse repetition frequency of one hertz as described.

Titanium nitride-coated titanium sheets, for example, served for the determination of the electrochemical properties, having been investigated in a half cell arrangement with 0.15M NaCl as the electrolyte. A smooth platinum sheet served as cooperating electrode; an AgCl electrode was employed as the reference electrode. The electrodes were connected to a potentiostat and the potential values were converted and related to the potential of the reversible hydrogen electrode (H$_2$ electrode). The electrodes thereby set a potential of $\phi/H_{2\,rev}=0.89$ V. (The specification $\phi/H_{2\,rev}$ denotes a potential referred to the reversible hydrogen electrode.) Under potentio-dynamic load, with a voltage rate of change of ten millivolts per second (10 mV/$_s$), one observed a constant current in the center of the interval $0 \leq \phi/H_{2\,rev} \leq 1$ V. Therefrom a double layer capacitance of 68 mF/cm$^2$ occurred at the beginning of the load, and this did not change over a load duration of eighty-eight hours (88 h). The investigations showed that no corrosion occurred up to a potential of 1.1 V; the electrodes are thus sufficiently stable.

The roughened surface layer at the active region can be produced by roughening the exterior metallic surface of the passive electrode at the active region to provide at least twice the area of contact with bodily fluids as would be provided by a smooth metal surface of configuration corresponding to that of the active region. The roughened surface may be permeated by bodily fluids to a depth between about one micrometer (one micron) and about one hundred micrometers, this depth being termed the "layer thickness".

The active region may also be comprised of activated carbon with a microporous exposed surface permeated by bodily fluids to a depth between about one micrometer (one micron) and about one hundred micrometers, this depth being termed the "layer thickness". Within the scope of the present disclosure, an activated surface is understood to mean a surface with a microporous, i.e., a roughened surface.

The term "mixed potentials" refers to potentials produced because of the presence of different materials—i.e. material associated potentials.

Although modifications and changes may be suggested by those skilled in the art, it is the intention of the inventors to embody within the patent warranted hereon all changes and modifications as reasonably and properly come within the scope of their contribution to the art.

We claim as our invention:

1. A bipolar electrode system for medical applications comprising an implantable heart pacemaker with an insulated flexible conductor system having at least one active electrode, a passive electrode disposed along the conductor system at an interval from the active electrode, and means for providing selected double layer capacitance at a phase boundary between a surface layer of said passive electrode and surrounding body fluids without substantial impairment of the flexibility of said conductor system, said means including a carrier material and an active region connected therewith forming said passive electrode, at least said active region of said passive electrode forming said surface layer exposed to said body fluids and providing said double layer capacitance at the phase boundary with the body fluids in the range of from about 10 millifarads per centimeter squared to about 100 millifarads per centimeter squared as measured at one hertz and said surface layer having a length along said conductor system selected for maintaining flexibility of said conductor system.

2. A bipolar electrode system as claimed in claim 1 wherein the surface layer is formed by a roughened surface of the passive electrode.

3. A bipolar electrode system as claimed in claim 1 wherein the active region of the passive electrode comprises sintered material having high porosity and a large internal surface area at least at a surface region providing said surface layer.

4. A bipolar electrode system as claimed in claim 1 wherein the surface layer is comprised of activated carbon with a porous microstructure.

5. A bipolar electrode system as claimed in claim 1 wherein the surface layer is comprised of a porous layer consisting of a carbide, nitride or carbonitride of at least one of the metals titanium, vanadium, zirconium, niobium, molybdenum, hafnium, tantalum or tungsten.

6. A bipolar electrode system as claimed in claim 1 wherein the surface layer is comprised of a porous layer consisting of a material selected from the group consisting of a carbide, nitride or carbonitride of at least one of the metals titanium, vanadium, zirconium, niobium, molybdenum, hafnium, tantalum and tungsten, and wherein a dense nonporous layer of a material corresponding to that of the porous layer is situated between the carrier material and said porous layer.

7. A bipolar electrode system as claimed in claim 6 wherein the dense nonporous layer has a layer thickness between about two microns and about ten microns.

8. A bipolar electrode system as claimed in claim 1 wherein the surface layer has a layer thickness between one micron and 100 microns.

9. A bipolar electrode system as claimed in claim 1 wherein the surface layer has a layer thickness between one micron and 100 microns, and wherein a dense nonporous layer of a material corresponding to that of the porous layer is situated between the carrier material and said porous layer.

10. A bipolar electrode system as claimed in claim 1 wherein the surface layer has a layer thickness between about five microns and about twenty microns.

11. A bipolar electrode system as claimed in claim 1 wherein the surface layer has a layer thickness between about five microns and about twenty microns, and wherein a dense nonporous layer of a material corresponding to that of the porous layer is situated between the carrier material and said porous layer, said dense nonporous layer having a layer thickness between about two microns and about ten microns.

* * * * *